(12) United States Patent
Schweitzer

(10) Patent No.: US 7,002,170 B2
(45) Date of Patent: Feb. 21, 2006

(54) RADIATION DEVICE

(75) Inventor: Bert Schweitzer, Korschenbroich (DE)

(73) Assignee: Arccure Technologies GbmH, Lippstadt (DE)

( * ) Notice: Subject to any disclaimer, the term of this patent is extended or adjusted under 35 U.S.C. 154(b) by 96 days.

(21) Appl. No.: 10/479,022

(22) PCT Filed: May 18, 2002

(86) PCT No.: PCT/EP02/05519

§ 371 (c)(1),
(2), (4) Date: Nov. 25, 2003

(87) PCT Pub. No.: WO02/097828

PCT Pub. Date: Dec. 5, 2002

(65) Prior Publication Data

US 2004/0149936 A1 Aug. 5, 2004

(30) Foreign Application Priority Data

May 26, 2001 (DE) .............................. 101 25 770

(51) Int. Cl.
*H05B 31/04* (2006.01)
(52) U.S. Cl. .................................. 250/504 R; 34/278
(58) Field of Classification Search ............ 250/504 R; 34/278
See application file for complete search history.

(56) References Cited

U.S. PATENT DOCUMENTS

| | | | |
|---|---|---|---|
| 3,986,018 A | 10/1976 | Ishii | |
| 4,015,340 A | 4/1977 | Treleven | |
| 4,560,883 A * | 12/1985 | Kerschgens | ............. 250/504 R |
| 4,591,724 A | 5/1986 | Fuse | |
| 5,864,144 A * | 1/1999 | Laine | ..................... 250/504 R |
| 6,621,087 B1 | 9/2003 | Bisges | |
| 6,646,278 B1 * | 11/2003 | Schwarz et al. | ........ 250/504 R |

FOREIGN PATENT DOCUMENTS

| | | |
|---|---|---|
| DE | 196 51 977 A1 | 12/1996 |
| WO | WO 98 54525 | 12/1998 |

* cited by examiner

*Primary Examiner*—John R. Lee
*Assistant Examiner*—Paul M. Gurzo
(74) *Attorney, Agent, or Firm*—Cohen, Pontani, Lieberman & Pavane

(57) ABSTRACT

The invention relates to an irradiation device for irradiating objects, comprising a housing having an outlet for the electromagnetic radiation directed at an object to be irradiated and at least one long radiation source for the electromagnetic radiation arranged in the housing. In order to enable bigger irradiation widths in an irradiation device, more particularly in a UV irradiation device, without deformation of the radiation source, at least one of the radiation sources in the irradiation device is rotationally arranged about its longitudinal axis.

11 Claims, 4 Drawing Sheets

RADIATION DEVICE

PRIORITY CLAIM

This is a U.S. national stage of application No. PCT/EP02/05519, filed on 18 May 2002. Priority is claimed on that application and on the following application: Country: Germany, Application No.: 101 25 770.8, Filed: 26 May 2001.

BACKGROUND OF THE INVENTION

1. Field of the Invention

The invention relates to an irradiation device for irradiating objects, in particular with ultraviolet and/or infrared and/or visible electromagnetic radiation, comprising a housing which comprises an outlet aperture for electromagnetic radiation, which outlet aperture is aligned to the object to be irradiated, as well as comprising at least one elongated radiation source, arranged in the housing, for electromagnetic radiation. Furthermore, the invention relates to an operating system for a radiation source according to the invention.

2. Description of the Related Art

Irradiation devices, in particular for UV light, are used for photochemically influencing irradiated objects. Important applications include the curing of printing inks, adhesives and coatings, as well as sterilization and medical irradiation. In particular for applications in the context of wooden board materials and floor coverings, UV irradiation devices with very high radiation outputs are used, with the irradiation width ranging up to several meters.

In UV irradiation devices, above all gas discharge lamps are used as radiation sources, in which gas discharge lamps a plasma is generated by the vaporization of metals. The lamps essentially comprise a tubular glass body, two electrodes, two foil fuse-ins as well as two lamp bases. Depending on the lamp type, the operating temperatures at the glass body can reach between 700° C. and 900° C.

All known elongated UV irradiation devices comprise a radiation source, suspended at both ends, which radiation source can be partly enveloped by a reflector.

The radiation sources are designed such that the energy absorbed by the glass is released by free convection and by radiation. An equilibrium between the absorbed energy quantity and the released energy quantity would occur at a temperature of the glass body of approx. 800° C. However, in practical application, the reflectors and the housing of the UV irradiation device impede this state. Reflection of heat radiation, and at times heat accumulation, can occur near the radiation source.

In order to overcome this problem, attempts have been made to set the temperature of the radiation source within the optimal operating range by means of improved air cooling systems. However, such arrangements are associated with a disadvantage that even with optimal cooling of the freely suspended irradiation source, i.e. an irradiation source which is only held by its end, beyond a critical electrical energy level in combination with a critical design length, the temperature of the glass body is such that all known radiation sources suffer deformation as a result of gravitational forces. Such sagging is evident in all irradiation sources, not just in UV radiation sources. Due to creep action in the glass body, whose operating temperature is just slightly below the temperature where material assumes a plastic state, all such radiation sources sooner or later suffer deformation. This particularity is already taken into account when the housing shape and the distance to the object to be irradiated are designed. However, if the deformation becomes excessive, then the plasma arising in the lamp can establish contact with the glass at a point. Such contact causes overheating and consequent destruction of the glass body of the radiation source.

In order to reduce deformation it is thus necessary according to the state of the art to reduce the design length of irradiation devices, in particular of UV irradiation devices, and at the same time to reduce the electrical output in the case of longer design lengths. According to the state of the art, large irradiation widths require several irradiation devices to be arranged side by side.

SUMMARY OF THE INVENTION

It is thus the object of the invention to create an irradiation device, in particular a UV irradiation device which allows larger irradiation widths without there being any deformation of the radiation source.

In an radiation device of the type mentioned in the introduction, this object is met in that at least one of the radiation sources in the irradiation device is arranged so as to be rotatable on its longitudinal axis.

Rotation of the radiation source on its longitudinal axis evens out the influence which gravitational forces have on creep action in the material of the radiation source. Since, with justifiable expenditure on cooling, operating temperatures can only be reduced to a certain extent, the invention is based on the elimination of the damaging effects of the forces acting upon the radiation source. This is achieved in that as a result of rotation, there is a continuous change in the direction of the gravitational forces which act on the material.

In the case of free convection, the temperature at the upper side of the radiation source is higher than the temperature at its lower side, because the upper side is heated up more by the upward-flowing air. As a result of this, the upper side may be subjected to local overheating which can destroy the radiation source. In order to prevent such destruction, radiation sources are designed according to the critical temperature at the upper side. By rotating the lamp, it can be operated at a higher specific output because the region which is exposed to the highest temperatures continuously changes.

According to the invention it is possible for several radiation sources to be arranged axially-parallel to each other in one irradiation device, with at least one being arranged so as to be rotatable on its longitudinal axis. Preferably however, all the radiation sources which are arranged in the irradiation device are rotatable. In this case, the radiation sources are advantageously connected to a common drive. The connection can for example be established by way of a belt transmission or a planetary gear arrangement.

In order to prevent damage to the body of the radiation source, which body is normally made of glass, the two ends of each rotatable radiation source are accommodated in a rotatably held seat arrangement, with at least one of the two seat arrangements of each radiation source being connected to a drive. If both seat arrangements of a radiation source are connected to a drive, torsion of the body of the radiation source can be substantially prevented as a result of the driving torque. The driving force for rotating the radiation sources can for example be by pneumatic, electric or manual means. However, in the case of short radiation sources, up to approx. 2 m in length, it is sufficient if the drive only engages one end.

In particular, in the case of radiation sources which only rotate in one specified direction it is advantageous if the power which is required for their operation is supplied in a contactless arrangement, for example by way of electromagnetic radiation (microwave excitation). As an alternative, a conventional power supply by way of sliding contacts is also possible.

If rotation of the radiation sources involves regular changes in direction, the electrical power can also be supplied by way of flexible cables, provided the angles of rotation in both directions are balanced.

From DE 199 16 474 A1, an irradiation device comprising an elongated radiation source for irradiating objects with UV radiation is known, whose housing comprises an outlet aperture aligned to the object to be irradiated. For the purpose of heat dissipation, the device comprises a cooling system in which a cooling-gas flow for the forced circulation cooling of the radiation source in the interior of the housing is circulated by fan force and re-cooled by way of a heat exchanger. The fan arrangement is constituted by several radial fans arranged so as to be distributed along the length of the radiation source, with the axes of these fans being aligned perpendicular to the radiation source. The cooling-gas which flows in by way of a lateral channel first flows around the casing of the radiation source and then flows through a longitudinal slit in the crown region of the reflector which is arranged above the radiation source, into a suction chamber which is arranged upstream of the fan.

This cooling system is associated with a disadvantage in that several radial fans, distributed along the length of the radiation source, are required for effective cooling. Furthermore, the design height which results from the vertical arrangement of the radial fans can render the use of the irradiation device difficult or even impossible where the available space is restricted.

An irradiation device for irradiating objects with electromagnetic radiation according to the invention includes a housing having an outlet aperture for electromagnetic radiation, which outlet aperture is aligned to the object to be irradiated, as well as at least one elongated radiation source, arranged in the housing, for electromagnetic radiation. The irradiation device comprises at least one admission channel and at least one discharge channel for cooling-gas, wherein each channel comprises a cooling-gas aperture which extends in the direction of the elongated radiation source along the length of the radiation source. The radiation source is arranged between the admission channel and the discharge channel, and at least one opposite surface partly envelopes the radiation source by forming a gap which becomes narrower in the direction towards the cooling-gas aperture of the discharge channel. Particularly effective cooling for the elongated radiation source is achieved by separating each channel from the interior space of the housing of the radiation device by means of a flow resistor, in particular a sieve, and by forming one of the channels as an integral part of an elongated barrier which at least partly masks the direct path of the rays from the radiation source to the object to be irradiated.

The narrowing gap between the radiation source and the opposite surface increases the flow speed of the cooling-gas from entry to the gap to entry to the discharge channel. This increase in speed prevents the flow from separating from the radiation source and thus ensures that the side of the radiation source which faces away from the admission channel is also always exposed to the flow of cooling-gas.

Preferably, when viewed from the outlet aperture for radiation, the discharge channel is arranged in front of the radiation source, while the admission channel is arranged behind the radiation source. Cooling the radiation source provides an additional safeguard against deflection. The cooling-gas, in particular air, which is fed to the discharge channel, preferably at its face, in conjunction with the sieve generates even overpressure along the entire length of the radiation source. The sieve at the discharge channel, which is preferably connected at its face with a negative-pressure generator, evens out the negative pressure along the entire length of the radiation source.

Improved cooling of the underside of the radiation source can be achieved in that in particular the discharge channel forms an integral part of the elongated barrier which at least partly masks the direct path of the rays from the irradiation source to the object to be irradiated, wherein each opposite surface for forming the narrowing gap is formed by the surface of the barrier or by reflectors which are arranged between the barrier and the radiation source. The surface of the barrier or of the reflectors partly envelopes the radiation source and forms the gap which becomes narrower in the direction of the cooling-gas aperture. The narrowing gap between the radiation source and the barrier increases the flow speed of the cooling-gas from entry into the gap to entry into the discharge channel.

As an alternative, when viewed from the outlet aperture for the radiation, the discharge channel can be arranged behind the radiation source. The reflectors which are arranged behind the radiation source can partly envelope the radiation source as opposite surfaces, thus forming the gap which narrows in the direction of the cooling-gas aperture.

In order to generate an equilibrium of forces in the body of the radiation source, rotation of the radiation source can periodically change direction and/or be interrupted. Interruption of rotation combined with a change in rotary direction is advantageous where continuous rotation is undesirable.

If the direction of rotation of the radiation source is always changed after partial rotation of the radiation source by at least 180°, then each point of the body of the radiation source experiences the gravitational forces acting upon it, once as a positive and once as a negative force vector, to almost the same extent. Thus any deformation of the radiation source, which deformation occurs during slow rotation, is always reversed again. Advantageous rotational speeds of the radiation source range from 0.1 to 0.2 r/s.

In order to keep deformation at an equilibrium, the rotational speed of the radiation source should be kept constant after startup. This ensures that each point of the body of the radiation source is exposed for the same period to the same gravitational forces, both in negative and in positive direction.

DETAILED DESCRIPTION OF THE PREFERRED EMBODIMENTS

Figure 1:
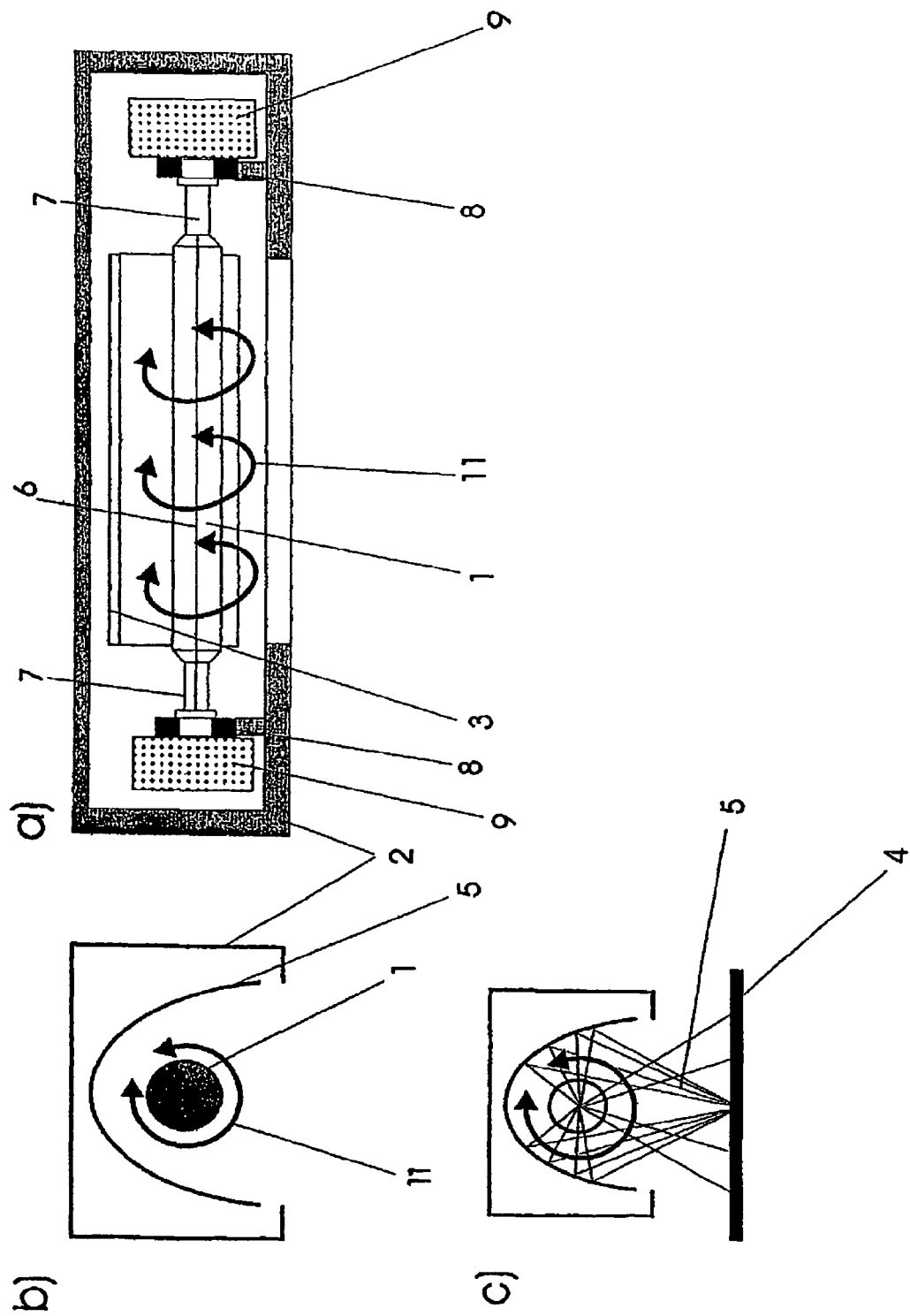
FIGS. 1a–c two diagrammatic front views and a diagrammatic lateral view of a first embodiment of a UV irradiation device according to the invention.

FIG. 1a) shows a tubular elongated radiation source 1 which is arranged within a housing 2 between a reflector 3 and the object 4 to be irradiated. The path of the rays 5 shown in FIG. 1c) leads to the object 4, partly directly from the radiation source 1, and partly indirectly by way of the reflector 3. The radiation source 1 is arranged in the housing 2 of the irradiation device such that it is rotatable on its longitudinal axis 6. The ends 7 of the radiation source are held by seat arrangements 8 which are held so as to be rotatable. The driving force for rotating the radiation source 1 is provided by the two drives 9 and the gear arrangement (not shown in detail) arranged therein. The direction of rotation of the radiation source, which direction is indicated by the arrow 11 in FIGS. 1a)–c) can be changed by means of a reversing-control system (not shown) which is known per se.

Figure 2:
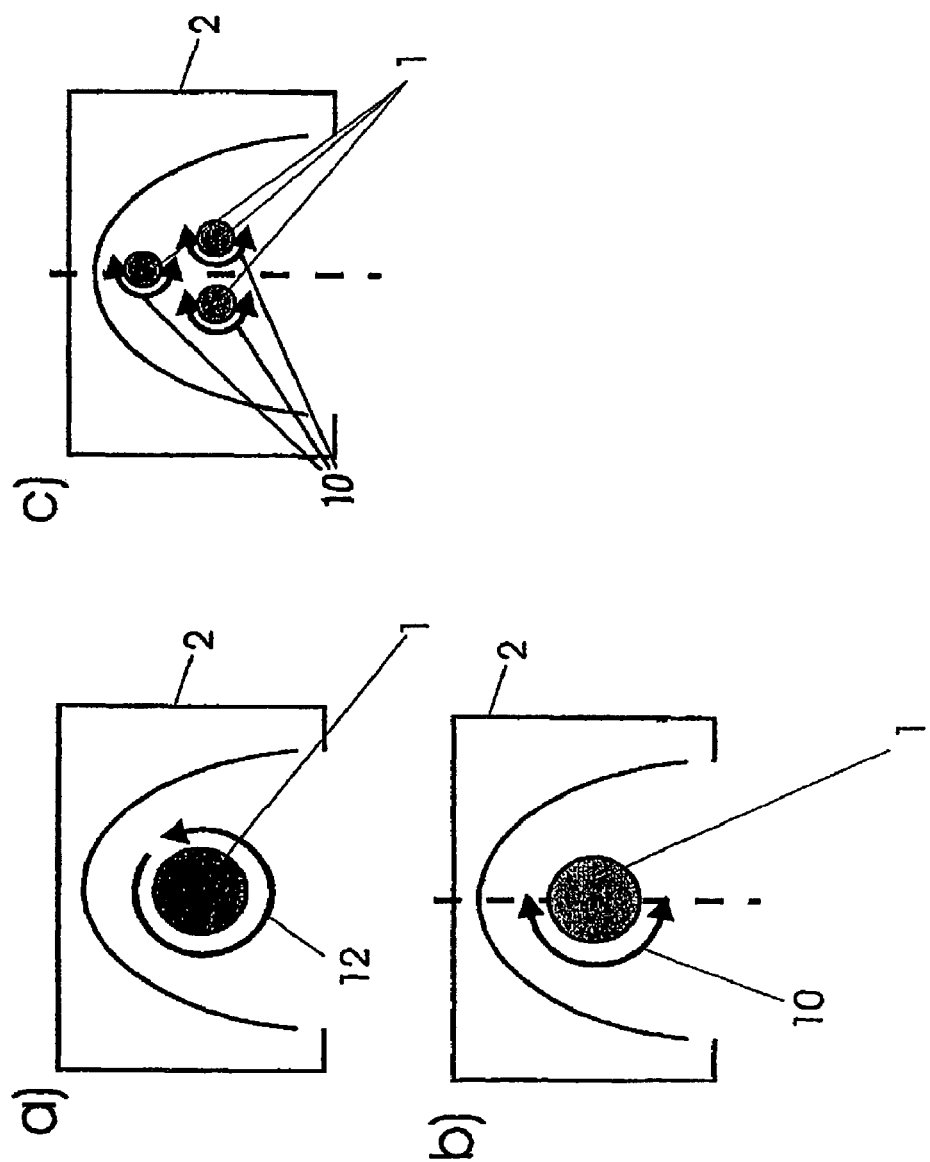
FIGS. 2a, b two further diagrammatic front views of the UV irradiation device according to FIG. 1.
FIG. 2c a diagrammatic front view of a second embodiment of a UV irradiation device according to the invention.

FIGS. 2a, b show different operating modes of the irradiation device according to FIG. 1. In FIG. 2a) the arrow 12 indicates continuous rotation of the radiation source in a defined direction at a constant rotational speed of 0.1 r/s. In FIG. 2b), the arrow 10 indicates that after partial rotation of the radiation source by at least 180°, the direction of rotation changes each time. FIG. 2c) shows an irradiation device in which a total of 3 radiation sources 1 concurrently rotate on their longitudinal axes 6, with the arrows 10 indicating that after partial rotation by 180°, the rotational direction of the radiation sources changes each time.

Figure 3:
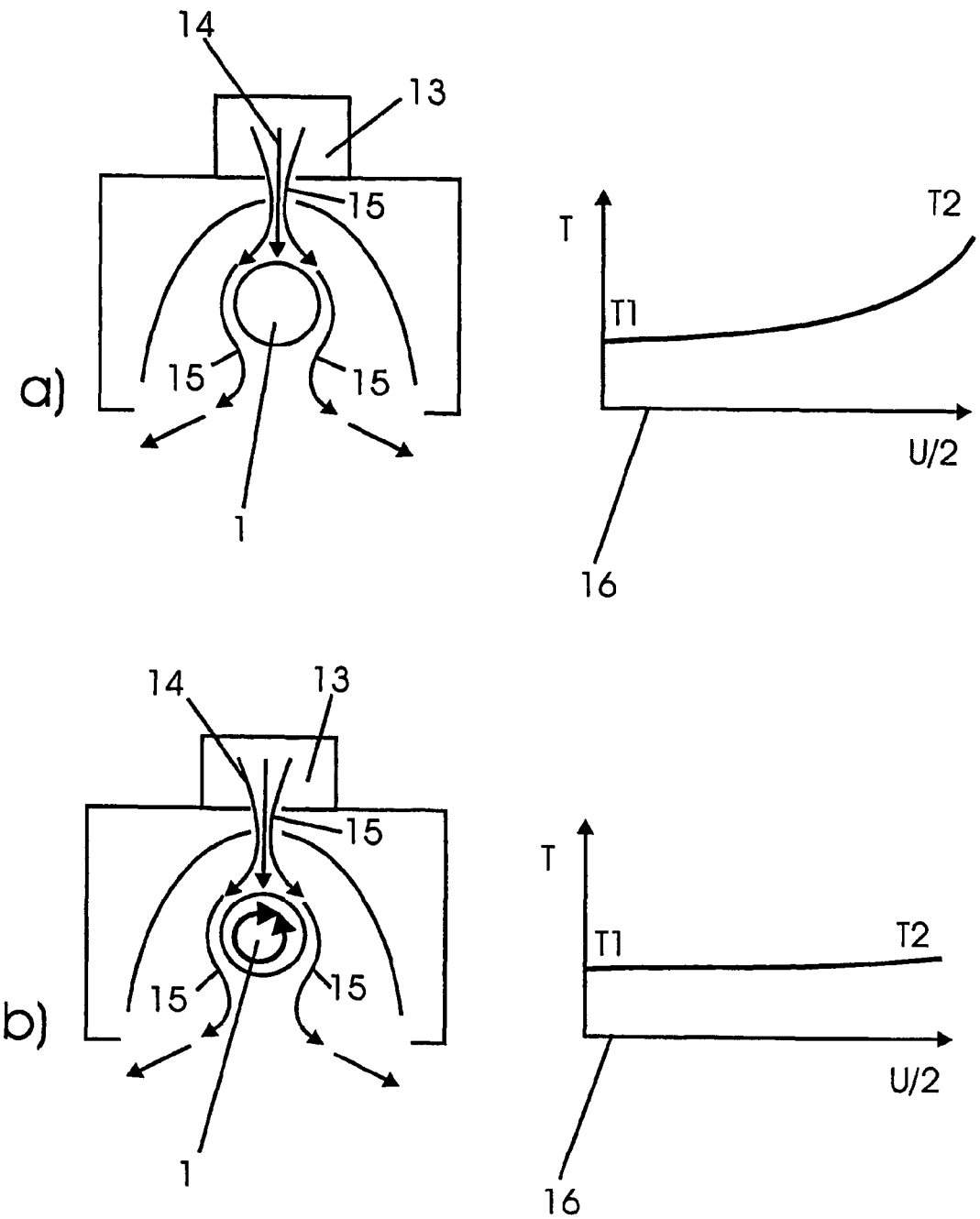
FIGS. 3a, b a diagrammatic view of the operation of the invention, taking into account a cooling-air flow 3.

FIG. 3a) shows an irradiation device comprising an admission channel 13 for cooling-air. Towards the bottom the admission channel 13 comprises an air inlet aperture 15 which extends at least along the length of the radiation source, with the air inlet aperture 15 leading to the interior of the housing 2. Advantageously, the air inlet aperture 15 is located perpendicularly above the radiation source 1. The cooling-air flow 14 leaves the air inlet aperture 15 in the direction of the radiation source 1. If the radiation source 1 is not rotated, the temperature T1 at the upper side of the radiation source 1 is considerably lower than the temperature at its lower side, where the air flow 15 moves away from the radiation source 1. In that region the temperature T2 is considerably higher. This connection is shown in the diagram 16 which shows the increase of the temperature over half the circumference of the radiation source 1 from the lower side to the upper side.

If the radiation source 1 is rotated continuously as indicated in FIG. 3b), the temperature differences between the upper side and the lower side of the radiation source 1 are considerably smaller. In the diagram 16 showing the temperature distribution over the circumference of the continuously rotating radiation source, T1 is the temperature at the upper side, and T2 is the temperature at the lower side of the radiation source, where the air stream separates.

Figure 4:
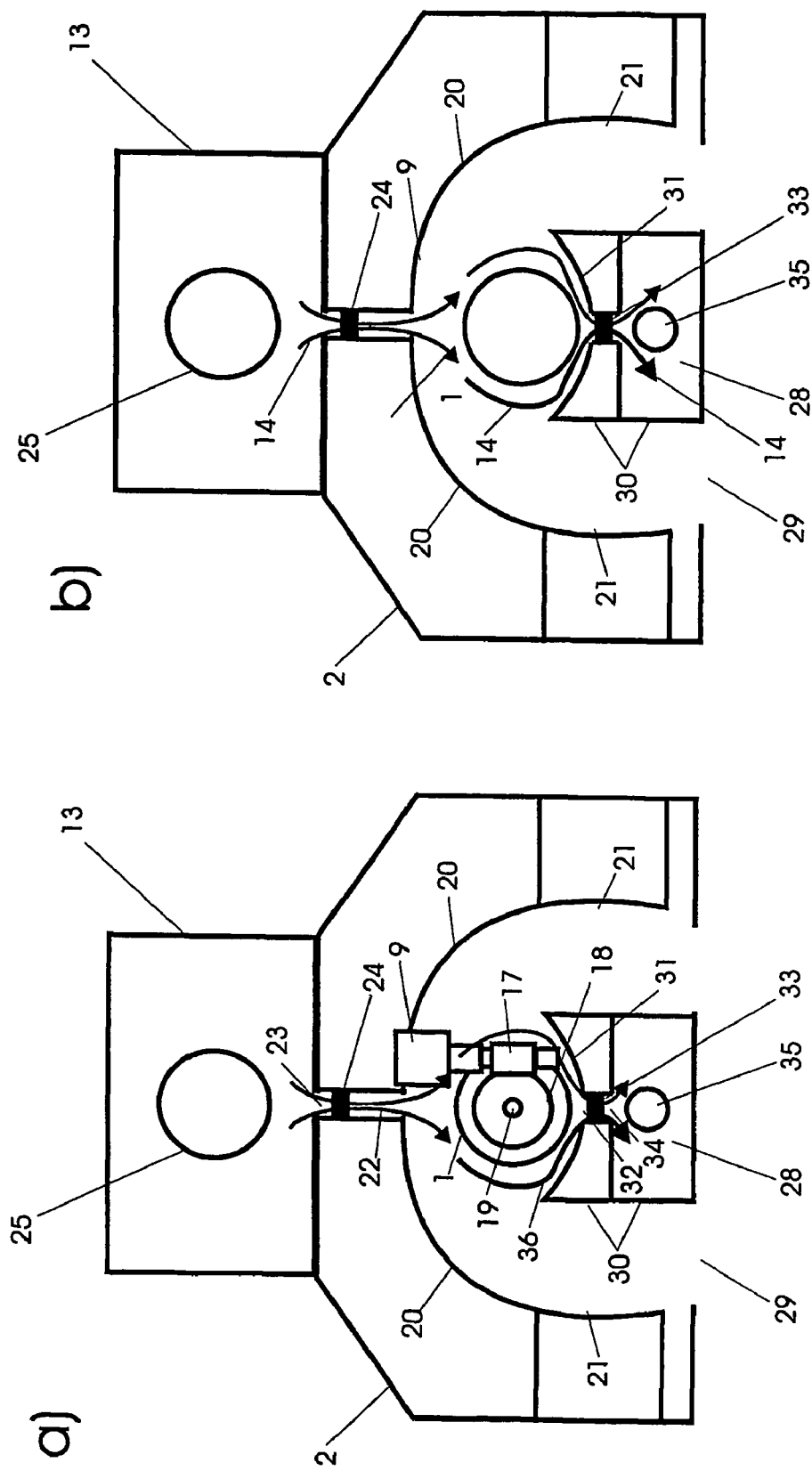
FIGS. 4a, b a diagrammatic front view of a third embodiment of a UV irradiation device according to the invention with a particularly effective cooling device.

An irradiation device according to FIG. 4 features effective cooling for both the lower side and the upper side of the radiation source 1. The radiation source 1, which in the embodiment shown is a UV lamp, is rotatably arranged in the housing 2. A screw shaft 17 of the electrical drive 9 intermeshes with a toothed wheel 18 which in a central aperture 19 accommodates one of the ends 7 of the radiation source 1.

The reflector 3 comprises two upper reflector elements 20 which extend along the entire length of the radiation device, and comprises two lower reflector elements 21. The two upper reflector elements 20 end in the region of an imaginary longitudinal mid-plane through the irradiation device, spaced apart from each other so as to form an air inlet slit 22. On the upper side of the housing 2 there is an admission channel 13 for the cooling-air. The admission channel 13 extends at least along the entire length of the air inlet slit 22. At its lower side the admission channel 13 comprises a cooling-air aperture 23 which covers the air inlet slit 22. A fine-meshed flow sieve 24 is in place between the air inlet slit 22 and the cooling-air aperture 23.

On the rear face of the admission channel 13 there is an inlet 25 by way of which the cooling-air reaches the admission channel 13. The flow sieve 24 evens out the pressure of the cooling-air along the entire length of the air inlet slit 22, thus resulting in even cooling of the radiation source along its entire length.

In the irradiation device according to FIG. 4, the usually occurring separation (explained by means of FIG. 3) between the cooling-air and the radiation source 1 is effectively prevented by means of an additional discharge channel 28. When viewed from the outlet aperture 29 for radiation, the discharge channel 28 is located in front of the radiation source 1 on the imaginary longitudinal mid-plane through the radiation device. The discharge channel 28 forms an integral part of an elongated barrier, overall designated 30, with the barrier 30 at least partially masking the direct path of the rays from the radiation source 1 to the object to be irradiated. For this purpose, the barrier comprises reflector elements 31 of curved cross-section, which together form an elongated trough which partly envelopes the radiation source 1 at its lower surface.

The reflector elements 31, which are spaced apart from each other, form an air outlet slit 32 which extends along the entire length of the radiation source 1. The air outlet slit 32 is separated from a cooling-air aperture 34 of the discharge channel 28 by a further flow sieve 33. The cooling-air aperture 34 also extends along the entire length of the radiation source 1. The flow sieve 33 also causes evening out of the pressure relationships at the discharge channel 28; however in this case it is related to the negative pressure present in the discharge channel 28. The negative pressure is for example generated by a vacuum pump (not shown) which is connected on the rear face at an outlet 35 of the discharge channel 28. This negative pressure can however also be generated by a fan arrangement whose suction side is connected to the discharge channel, and whose positive pressure side is connected to the admission channel. In the circuit which is closed in this way, cooling-air is additionally filtered and re-cooled.

FIG. 4 shows that the reflector elements 31, which form the surface of the barrier, form a gap 36 which narrows in the direction of the discharge channel 28. Consequently, the cooling-gas flow 14 which enters the gap 36 on both sides of the radiation source 1 is accelerated, and in this way separation of the cooling-gas flow 14 from the radiation source 1 at the lower side of the radiation source 1 is effectively prevented. Despite such effective cooling of the lower side of the radiation source 1 by means of the discharge channel 28 which is integrated in the barrier, due to heat absorption of the cooling-air flow, the temperature at the lower side of the radiation source 1 is still higher. Although this temperature difference is clearly less pronounced than is the case in an irradiation device according to FIG. 3a, for further evening out of the temperatures it is expedient if the radiation source is arranged so as to be rotatable, and if the radiation source is rotated during operation, as shown in FIG. 4a).

The cooling device described can however also be used to advantage in radiation devices with statically arranged radiation sources, as shown in FIG. 4b).

What is claimed is:

1. An irradiation device for irradiating objects with electromagnetic radiation, said device comprising:
    a housing having an interior and an outlet aperture;
    at least one elongate radiation source arranged in the housing;
    an admission channel having a cooling gas admission aperture extending parallel to said radiation source;
    a sieve located between said admission aperture and said interior of said housing;
    a discharge channel having a cooling gas discharge aperture extending parallel to said radiation source opposite from said admission aperture;
    a sieve located between said discharge aperture and said interior of said housing;
    a surface partly enveloping said radiation source and forming a gap which converges toward the cooling gas discharge aperture; and
    an elongate barrier between said radiation source and said outlet aperture, said barrier forming one of said channels, said barrier comprising curved reflector elements facing the radiation source.

2. An irradiation device as in claim 1 wherein said surface forming said gap is formed by said curved reflector elements.

3. An irradiation device as in claim 1 wherein each said elongate radiation source has a longitudinal axis and a pair of opposed ends, at least one said elongate radiation source being rotatable about its longitudinal axis.

4. An irradiation device as in claim 3 further comprising a pair of rotatably held seat arrangements accommodating respective said ends of each rotatable radiation source, and a drive connected to at least one of said radiation sources.

5. An irradiation device as in claim 3 wherein a plurality of said radiation sources are rotatable, said device further comprising a common drive for rotating said rotatable radiation sources.

6. An irradiation device 3 further comprising a contactless supply of power for operating at least one said elongate radiation source which is rotatable about its longitudinal axis.

7. A method for operating an irradiation device of the type comprising:
    a housing having an interior and an outlet aperture;
    at least one elongate radiation source arranged in the housing, each said elongate radiation source having a longitudinal axis and a pair of opposed ends, at least one said elongate radiation source being rotatable about its longitudinal axis;
    an admission channel having a cooling gas admission aperture extending parallel to said radiation source;
    a sieve located between said admission aperture and said interior of said housing;
    a discharge channel having a cooling gas discharge aperture extending parallel to said radiation source opposite from said admission aperture;
    a sieve located between said discharge aperture and said interior of said housing;
    a surface partly enveloping said radiation source and forming a gap which converges toward the cooling gas discharge aperture; and
    an elongate barrier between said radiation source and said outlet aperture, said barrier forming one of said channels, said barrier comprising curved reflector elements facing the radiation source;
    wherein said method comprises rotating each said rotatable radiation source and at least one of periodically changing the direction of rotation and rotating the radiation source in only one direction.

8. A method as in claim 7 wherein the direction of rotation is changed after each partial rotation of the radiation source by at least 180°.

9. A method as in claim 7 wherein each said rotatable radiation source is rotated in only one direction.

10. A method as in claim 9 wherein said rotation in one direction is interrupted.

11. A method as in claim 7 wherein each said rotatable radiation source is rotated at a constant rotational speed in a range between 0.1 and 0.2 r/s.

* * * * *